United States Patent
Shani et al.

(10) Patent No.: US 12,082,687 B2
(45) Date of Patent: Sep. 10, 2024

(54) APPARATUS FOR DETECTING ORAL DISEASES AND HAZARDS

(71) Applicant: PLAQLESS LTD, Yokneam Ilit (IL)

(72) Inventors: Yuval Shani, Pardes Chana Karkur (IL); Tamir Ygal, Eschar (IL)

(73) Assignee: PLAQLESS LTD, Yokneam Ilit (IL)

(*) Notice: Subject to any disclaimer, the term of this patent is extended or adjusted under 35 U.S.C. 154(b) by 694 days.

(21) Appl. No.: 17/257,616

(22) PCT Filed: Jul. 10, 2019

(86) PCT No.: PCT/IL2019/050771
§ 371 (c)(1),
(2) Date: Jan. 4, 2021

(87) PCT Pub. No.: WO2020/012476
PCT Pub. Date: Jan. 16, 2020

(65) Prior Publication Data
US 2021/0290071 A1    Sep. 23, 2021

Related U.S. Application Data

(60) Provisional application No. 62/697,436, filed on Jul. 13, 2018.

(51) Int. Cl.
*A46B 15/00* (2006.01)
*A46B 5/00* (2006.01)
(Continued)

(52) U.S. Cl.
CPC ........ *A46B 5/0095* (2013.01); *A46B 15/0034* (2013.01); *A46B 15/0038* (2013.01);
(Continued)

(58) Field of Classification Search
CPC ............ A46B 15/0038; A46B 15/0036; A61C 17/221; A61C 17/22; G06T 7/529
See application file for complete search history.

(56) References Cited

U.S. PATENT DOCUMENTS

2002/0178032 A1    11/2002    Benn et al.
2004/0202356 A1    10/2004    Stookey et al.
(Continued)

FOREIGN PATENT DOCUMENTS

CN    105744911 A    7/2016
EP    1792581 A1    6/2007
(Continued)

OTHER PUBLICATIONS

Supplementary European Search Report issued in European Patent Application No. 19833807 dated Mar. 11, 2022.
(Continued)

*Primary Examiner* — Michael D Jennings
(74) *Attorney, Agent, or Firm* — MARSHALL, GERSTEIN & BORUN LLP

(57) ABSTRACT

The present invention relates to an apparatus comprising an insertion member configured to be inserted to a user's mouth. The insertion member comprises one or more illumination sources, configured to illuminate a part of the user's mouth when inserted thereinto; one or more imaging devices configured to capture images of the user's mouth interior; and a processing module configured to receive images from the one or more imaging devices, process the images to data, and detect oral and/or dental anomalies from the processed images and send the processed images and data via wireless or wired connection to a physician or professional doctor for further analysis.

9 Claims, 4 Drawing Sheets

(51) Int. Cl.
*A61B 1/00* (2006.01)
*A61B 1/06* (2006.01)
*A61B 1/24* (2006.01)
*A61B 5/00* (2006.01)
*A61C 9/00* (2006.01)
*G06F 18/214* (2023.01)
*G06T 7/00* (2017.01)
*G06T 7/529* (2017.01)
*A61C 17/22* (2006.01)

(52) U.S. Cl.
CPC ............ *A61B 1/00011* (2013.01); *A61B 1/06* (2013.01); *A61B 1/24* (2013.01); *A61B 5/0022* (2013.01); *A61B 5/0088* (2013.01); *A61B 5/4547* (2013.01); *A61C 9/0053* (2013.01); *G06F 18/214* (2023.01); *G06T 7/0012* (2013.01); *G06T 7/529* (2017.01); *A46B 2200/01* (2013.01); *A46B 2200/1066* (2013.01); *A61C 17/22* (2013.01); *G06T 2207/20081* (2013.01); *G06T 2207/30036* (2013.01); *G06V 2201/032* (2022.01)

(56) References Cited

U.S. PATENT DOCUMENTS

| | | |
|---|---|---|
| 2007/0280888 A1 | 12/2007 | Fujikawa et al. |
| 2008/0017787 A1 | 1/2008 | Okawa et al. |
| 2010/0015575 A1 | 1/2010 | Martin et al. |
| 2012/0171634 A1 | 7/2012 | Graham et al. |
| 2014/0272768 A1* | 9/2014 | Curry ................. A46B 15/0055 433/29 |
| 2015/0107034 A1 | 4/2015 | Shani et al. |
| 2016/0242652 A1 | 8/2016 | Van Putten et al. |
| 2016/0307323 A1 | 10/2016 | Wu et al. |
| 2016/0331498 A1* | 11/2016 | Follows ............... A61C 17/028 |
| 2017/0007215 A1* | 1/2017 | Podoly ............... A61B 10/0012 |
| 2018/0035896 A1 | 2/2018 | Nozaki |
| 2018/0137773 A1* | 5/2018 | Gatzemeyer ....... A46B 15/0002 |
| 2019/0200902 A1* | 7/2019 | El Kouby-Benichou .................... A61B 5/1127 |
| 2020/0146794 A1* | 5/2020 | Lee ........................ G16H 50/20 |

FOREIGN PATENT DOCUMENTS

| | | | |
|---|---|---|---|
| JP | 2014-133029 A | 7/2014 | |
| WO | WO-2013/001462 A2 | 1/2013 | |
| WO | WO-2014202250 A1 * | 12/2014 | ......... A46B 15/0004 |
| WO | WO-2018/001171 A1 | 1/2018 | |
| WO | WO-2018/029276 A1 | 2/2018 | |
| WO | WO-2018/172330 A1 | 9/2018 | |

OTHER PUBLICATIONS

International Application No. PCT/IL2019/050771, International Search Report and Written Opinion, dated Oct. 7, 2019.
International Application No. PCT/IL2019/050771, International Preliminary Report on Patentability, dated Nov. 17, 2020.
Office Action, Chinese patent application No. 201980046034.5, mailing date Jan. 15, 2024.

* cited by examiner

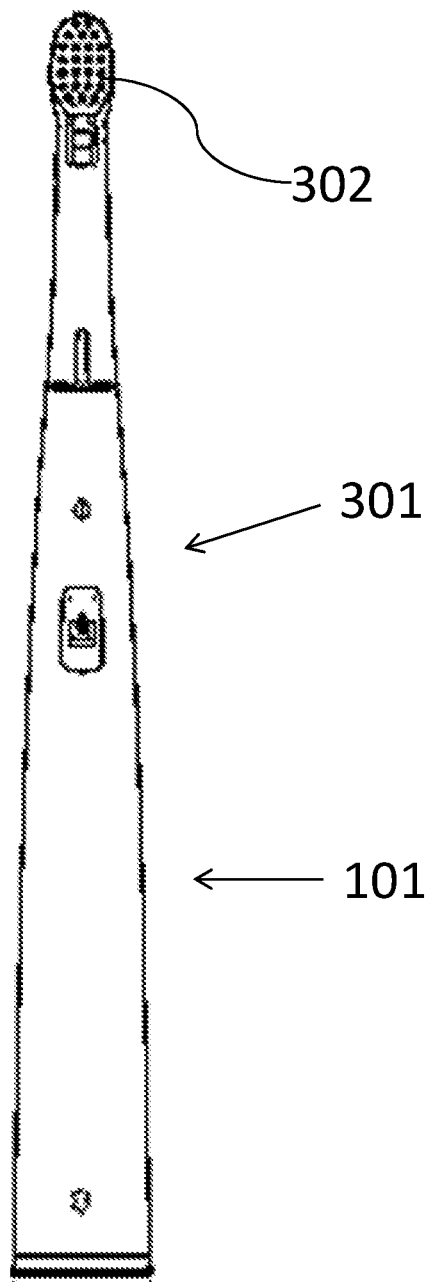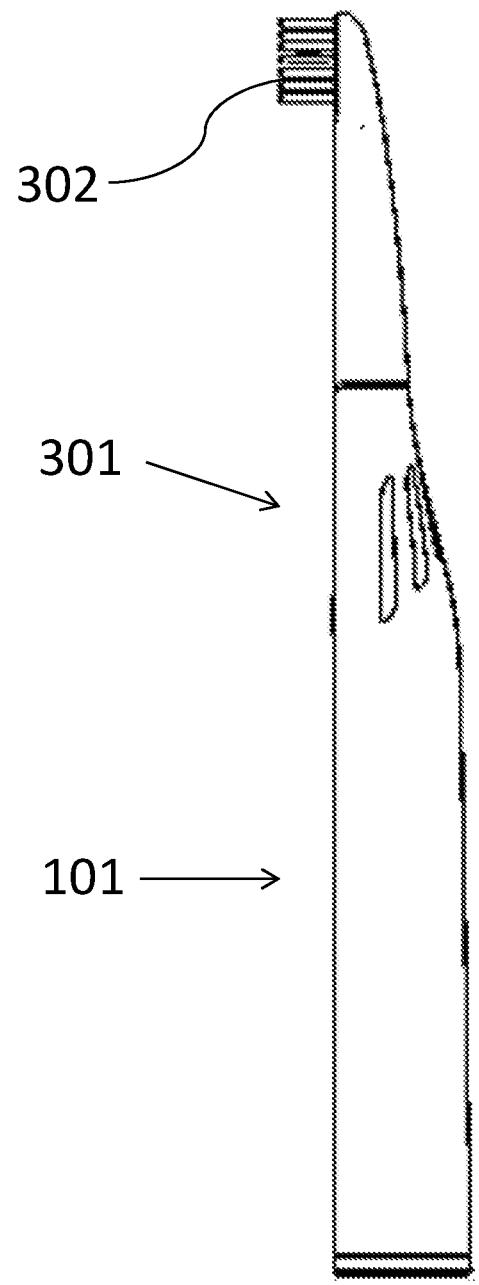
Fig. 3A
Fig. 3B

APPARATUS FOR DETECTING ORAL DISEASES AND HAZARDS

FIELD OF THE INVENTION

The present invention relates to the field of dental and oral health. More particularly, the invention relates to an apparatus for detecting dental and oral hazards such as gingivitis, cavities and oral cancer.

BACKGROUND OF THE INVENTION

Early detection of deceases and health hazards allow physicians to efficiently treat and prevent severe damage to a patient's health. This principle also applies to the field of oral (i.e. relating to the mouth) and dental (i.e. relating the teeth) deceases and hazards.

Typically, an individual isn't aware of formation of deceases and hazards inside the mouth, especially in stages that are considered early in the development thereof. Oral hazards are commonly discovered either when oral pain or anomalies occur, in which case the detection isn't early, or during a visit to the dentist that might also be too late.

It is therefore an object of the present invention to provide an apparatus for early detection of oral and dental hazards that can be used by a home user without any prior knowledge or knowhow in the field.

It is another object of the present invention to provide an apparatus for detection of oral and dental hazards that doesn't require visiting a physician.

Other objects and advantages of the invention will become apparent as the description proceeds.

SUMMARY OF THE INVENTION

The present invention relates to an apparatus for detecting oral deceases and hazards, comprising:
- an insertion member configured to be inserted into the mouth of a user;
- one or more illumination sources configured to illuminate a part of the user's mouth;
- one or more imaging devices configured to capture images of the user's mouth interior; and
- a processing module configured to receive images from said one or more imaging devices, process said received images and detect oral anomalies from the processed data.

According to an embodiment of the invention, the apparatus further comprises one or more communication devices able to communicate the processed data and analytics to a nearby computer, smartphone or any other storage device.

According to an embodiment of the invention, the apparatus is configured to convey the processed data to a physician, doctor or health professional for further analysis and medical opinion, e.g., via one or more networks, social media, or other communication configuration.

According to an embodiment of the invention, the received images are processed by the processing module using a proprietary algorithm and machine learning techniques.

According to an embodiment of the invention, the apparatus is provided on the distal end of a toothbrush handle.

According to an embodiment of the invention, at least one of the illumination sources is configured to provide ultraviolet light (in the UVA range), the one or more imaging devices comprises at least one fluorimeter, and the processing module further comprises a machine learning module which is configured to detect gingivitis by identifying patterns on the user's gums that are of an outstanding color, texture or shape, and mark them as areas with high probability of gingivitis.

According to an embodiment of the invention, the processing module further comprises a machine learning module for detecting the formation of early cavities by identifying tooth shapes and separating an image of a group of teeth to individual teeth, and is configured to detect unique patterns on each said individual tooth based on shape, texture and color and mark them as areas with high probability of cavity formation.

According to an embodiment of the invention, the processing module further comprises a machine learning module for detecting formation of oral cancer sores by identifying and eliminating teeth from images of the user's mouth and is configured to detect unique patterns in the remaining portion of the mouth based on shape, texture, and color.

According to an embodiment of the invention, the apparatus is wirelessly connected to a remote computerized device, e.g. a PDA, smartphone, cloud, server farm etc.

In another aspect, the present invention relates to a smart toothbrush comprising the apparatus for detecting oral deceases and hazards and a disposable toothbrush head.

BRIEF DESCRIPTION OF THE DRAWINGS

In the drawings:

FIGS. 3A and 3B schematically illustrate front and side view, respectively, of the apparatus of FIG. 1 on which a disposable toothbrush head is applied, according to an embodiment of the present invention.

DETAILED DESCRIPTION OF THE INVENTION

Reference will now be made to an embodiment of the present invention, examples of which are provided in the accompanying figures for purposes of illustration only. One skilled in the art will readily recognize from the following description that alternative embodiments of the structures and methods exemplified herein may be employed, mutatis mutandis, without departing from the principles of the invention.

Various oral and dental anomalies may be detected visually. For instance, biological cells (especially proteins) may be detected by using the fluorescence effect. Germs react to a light at a specific wavelength, thus they may be detected by exposing them to such light, capturing one or more images thereof and processing the one or more images. Furthermore, cavities in the early stage comprise a unique shape, size and color compared to the tooth surface (dental enamel). Image processing of such images may allow early detection of cavities. Moreover, oral cancer sores in the early stage have unique shapes and color compared to gums or tongue on which they are formed. Once again image processing may be utilized for early detection of oral cancer.

Figure 1:
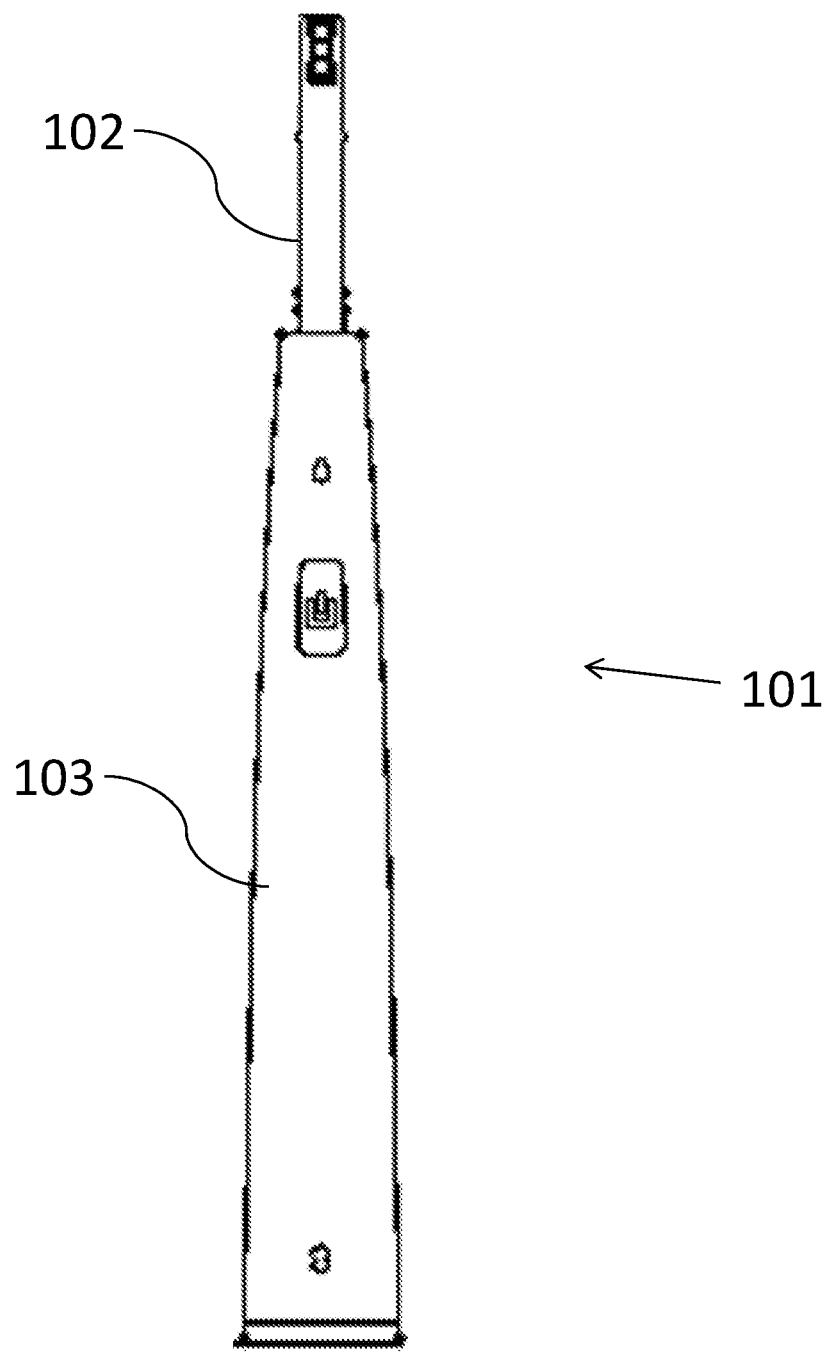
FIG. 1 schematically illustrates a front view of a home use apparatus for detection of oral and dental hazards, according to an embodiment of the present invention.
Figure 2:
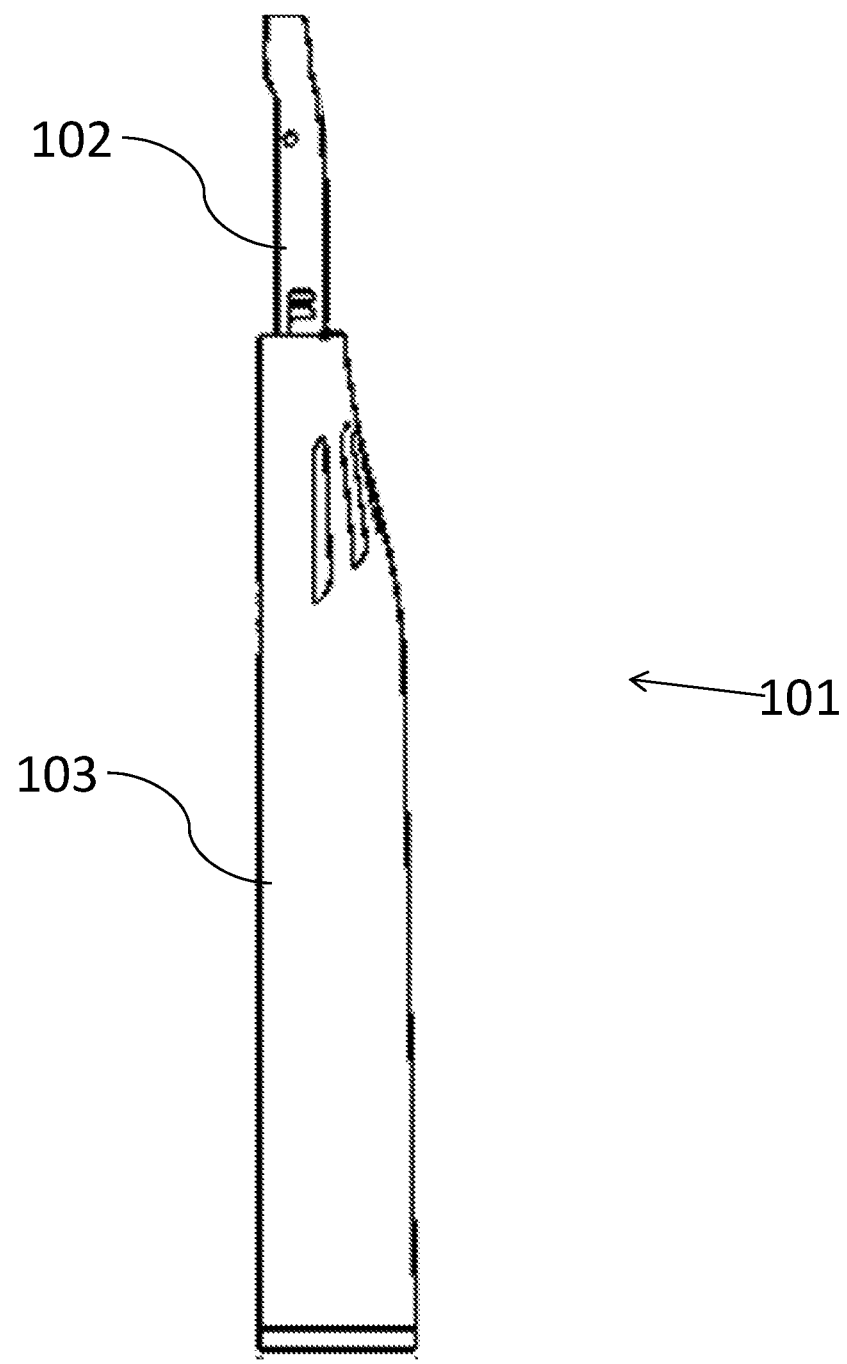
FIG. 2 schematically illustrates a side view of the home use apparatus of FIG. 1.

Accordingly, the present invention relates to an apparatus comprising an insertion member configured to be inserted to a user's mouth. The insertion member comprises one or more illumination sources, configured to illuminate a part of the user's mouth when inserted thereinto; one or more imaging devices configured to capture images of the user's mouth interior; and a processing module configured to receive images from the one or more imaging devices, process the images to data, and detect oral and/or dental anomalies from the processed images. FIGS. 1 and 2 schematically illustrate front and side views, respectively, of an apparatus 101 for detection of oral and dental hazards, according to an embodiment of the present invention, comprising an insertion member 102 provided at the distal end of a toothbrush handle 103.

According to an embodiment of the present invention, illumination sources 102 are configured to provide light in a specific wavelength close to the ultraviolet range (UVA range) suitable for detecting fluorescence effect, the imaging devices comprises a fluorimeter, and the processing module further comprises a machine learning module which detects the exact gums pattern by eliminating teeth and other elements of the mouth and is configured to detect gingivitis by identifying patterns on a user's gums that are of an outstanding color, texture or shape and mark them as areas with high probability of gingivitis.

According to another embodiment of the present invention, the processing module is configured to detect cavities by identifying tooth shapes and to separate an image of a group of teeth to individual teeth, and to detect unique patterns on each tooth based on shape, texture and color thereof. A machine leaning module is utilized for identifying changes in shape, color or texture on a tooth surface and that is outstanding from the rest of the tooth surface and could imply a formation of cavities.

According to yet another embodiment of the present invention, the processing module is configured to detect oral cancer. Oral cancer sores usually reside on the gums and tongue of a user and not directly on the teeth, therefore detecting oral cancer is performed by eliminating the teeth from images and searching the remaining portion of images of a user's mouths for unique patterns based on shape, texture and color. A machine leaning module is utilized for searching typical patterns that are common for sores and for identifying patterns that could indicate forming of oral cancer.

According to an embodiment of the present invention, the apparatus is connected (either wirelessly or in a wired manner) to a remote computerized device, e.g. a PDA, a smartphone, cloud, server farm, etc., which is configured to further process the images and provide a detection notification to the relevant physician. According to an embodiment of the present invention, only images that raise suspicion of oral or dental hazards are conveyed to the computerized device and the physician.

Figure 4A:
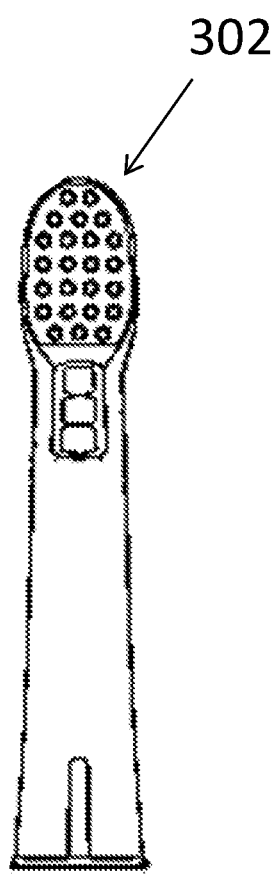
FIGS. 4A and 4B schematically illustrate enlarged views of FIGS. 3A and 3B, respectively.
Figure 4B:
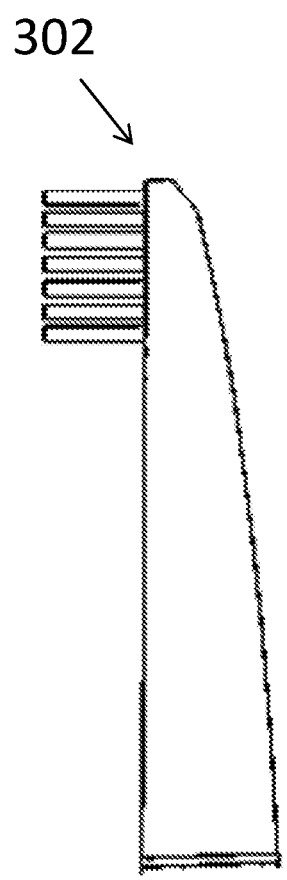

FIGS. 3A and 3B schematically illustrate front and side views, respectively, of a smart toothbrush 301, according to an embodiment of the present invention, comprising apparatus 101, the distal end of which is provided with a disposable toothbrush head 302. In this embodiment, when disposable head 302 is applied, the apparatus can be used for monitoring toothbrushing in addition to the functions mentioned above with relation to FIGS. 1 and 2. FIGS. 4A and 4B schematically illustrate enlarged views of FIGS. 3A and 3B, respectively, showing only the disposable head 302 that is adapted to be applied on the distal end of apparatus 101.

Although embodiments of the invention have been described by way of illustration, it will be understood that the invention may be carried out with many variations, modifications, and adaptations, without exceeding the scope of the claims.

The invention claimed is:

1. An apparatus for detecting oral deceases and hazards, comprising:
   a. an insertion member configured to be inserted into the mouth of a user;
   b. one or more illumination sources configured to illuminate a part of the user's mouth;
   c. one or more imaging devices configured to capture images of the user's mouth interior;
   d. a processing module, incorporating a machine learning module configured to receive images from said one or more imaging devices, process said received images using the machine learning to detect oral anomalies, including specific patterns indicative of various oral diseases, from the processed data;
   e. one or more communication devices configured to communicate the processed data and analytics to other device or system; and a smart toothbrush including a disposable toothbrush head over the insertion member.

2. An apparatus according to claim 1, wherein the other device or system is a nearby computer, smartphone or any other storage device.

3. An apparatus according to claim 1, wherein one or more networks, social media, communication configuration are used to convey the processed data to a physician, doctor or health professional for further analysis and medical opinion.

4. An apparatus according to claim 1, wherein the processing module employs a proprietary algorithm, configured for enhanced analysis and detection of oral diseases, in combination with machine learning techniques, to process the received images.

5. An apparatus according to claim 1 provided on the distal end of a toothbrush handle.

6. An apparatus according to claim 1, wherein at least one of the illumination sources is configured to provide ultraviolet light (in the UVA range), the one or more imaging devices comprises at least one fluorimeter, and the processing module is configured to detect gingivitis by identifying patterns on the user's gums that are of an outstanding color, texture or shape, and mark them as areas with high probability of gingivitis.

7. An apparatus according to claim 1, wherein the machine learning module is configured for detecting the formation of early cavities by identifying tooth shapes and separating an image of a group of teeth to individual teeth, and is configured to detect unique patterns on each said individual tooth based on shape, texture and color and mark them as areas with high probability of cavity formation.

8. An apparatus according to claim 1, wherein machine learning module is configured for detecting formation of oral cancer sores by identifying and eliminating teeth from images of the user's mouth and is configured to detect unique patterns in the remaining portion of the mouth based on shape, texture, and color.

9. An apparatus according to claim 1 connected to a remote computerized device e.g. a PDA, smartphone, cloud, server farm etc.

* * * * *